United States Patent
Schmidt et al.

(10) Patent No.: US 9,630,891 B2
(45) Date of Patent: *Apr. 25, 2017

(54) METHOD FOR CONVERTING HYDROCARBON FEEDSTOCKS INTO OLEFINIC PRODUCT FLOWS BY MEANS OF THERMAL STEAM CRACKING

(71) Applicant: Linde Aktiengesellschaft, Munich (DE)

(72) Inventors: Gunther Schmidt, Deisenhofen (DE); Helmut Fritz, Munich (DE); Stefanie Walter, Seehausen (DE)

(73) Assignee: Linde Aktiengesellschaft, Munich (DE)

( * ) Notice: Subject to any disclaimer, the term of this patent is extended or adjusted under 35 U.S.C. 154(b) by 87 days.

This patent is subject to a terminal disclaimer.

(21) Appl. No.: 14/420,633

(22) PCT Filed: Aug. 1, 2013

(86) PCT No.: PCT/EP2013/002298
§ 371 (c)(1),
(2) Date: Feb. 9, 2015

(87) PCT Pub. No.: WO2014/023407
PCT Pub. Date: Feb. 13, 2014

(65) Prior Publication Data
US 2015/0225313 A1   Aug. 13, 2015

(30) Foreign Application Priority Data
Aug. 9, 2012   (EP) .................................. 12005781

(51) Int. Cl.
*C07C 4/04*   (2006.01)
*C10G 9/36*   (2006.01)

(52) U.S. Cl.
CPC .................. *C07C 4/04* (2013.01); *C10G 9/36* (2013.01); *C10G 2400/20* (2013.01)

(58) Field of Classification Search
None
See application file for complete search history.

(56) References Cited

U.S. PATENT DOCUMENTS 2,017,874 A   10/1935   Sullivan
6,743,961 B2   6/2004   Powers
(Continued)

FOREIGN PATENT DOCUMENTS

CN   1529686 A   9/2004

OTHER PUBLICATIONS

English Translation of Chinese Application No. 201380040715.3 Examination Report dated Dec. 22, 2015, 6 pages.
(Continued)

*Primary Examiner* — Tam M Nguyen
(74) *Attorney, Agent, or Firm* — Lathrop & Gage LLP

(57) ABSTRACT

The invention relates to a process for converting feeds composed of hydrocarbons by thermal steamcracking to at least one olefin-containing product stream comprising at least ethylene and propylene, with at least partial conversion of the feeds in at least one first cracking furnace (1) and in at least one second cracking furnace (2). According to the invention, a fresh feed (B) is fractionated into at least one first and one second fresh feed fraction (B1, B2), and the first fresh feed fraction (B1) is conducted at least partly into the first cracking furnace (1) and the second fresh feed fraction (B2) at least partly into the second cracking furnace (2).

12 Claims, 2 Drawing Sheets

(56) References Cited

U.S. PATENT DOCUMENTS

2004/0039240 A1 2/2004 Powers
2004/0209964 A1 10/2004 Ansorge et al.
2008/0194900 A1 8/2008 Bhirud
2008/0223754 A1 9/2008 Subramanian et al.

OTHER PUBLICATIONS

PCT/EP2013/002298 English Translation of the International Preliminary Report on Patentability mailed Aug. 13, 2014, 6 pages.
PCT/EP2013/002298 English Translation of the International Search Report mailed Oct. 22, 2013, 3 pages.

METHOD FOR CONVERTING HYDROCARBON FEEDSTOCKS INTO OLEFINIC PRODUCT FLOWS BY MEANS OF THERMAL STEAM CRACKING

The present invention relates to a process for converting feeds composed of hydrocarbons by thermal steamcracking to at least one olefin-containing product stream comprising at least ethylene and propylene, with at least partial conversion of the feeds in at least one first cracking furnace and in at least one second cracking furnace.

Thermal steamcracking is a long-established petrochemical process. The standard target compound in thermal steamcracking is ethylene (also referred to as ethene), which is an important starting compound for a number of chemical syntheses.

The feeds used for the thermal steamcracking may be either gases such as ethane, propane or butane and corresponding mixtures or liquid hydrocarbons, for example naphtha, and hydrocarbon mixtures.

With regard to the specific apparatuses and reaction conditions used in thermal steamcracking, and with regard to the reactions which proceed and to details of refinery technology, reference is made to corresponding articles in reference works such as Zimmermann, H. and Walzl, R.: Ethylene, in: Ullmann's Encyclopedia of Industrial Chemistry, 6th ed. Weinheim: Wiley-VCH, 2005, and Irion, W. W. and Neuwirth, O. S.: Oil Refining, in: Ullmann's Encyclopedia of Industrial Chemistry. 6th ed. Weinheim: Wiley-VCH 2005. Processes for preparing olefins are also disclosed, for example, in U.S. Pat. No. 3,714,282 A and 6,743,961 B1, and 6,743,961 B2 includes a process for preparing olefins in which heavy oil is pretreated in a mild cracking process before it is conducted into a furnace for thermal cracking.

In addition, mention should be made here of US 2004/209964, which discloses that hydrocarbons which have a carbon number between 15 and 30 and have been produced by a Fischer-Tropsch synthesis and fractionated are hydrogenated and then thermally cracked under mild conditions. U.S. Pat. No. 2,017,874 A, in contrast, includes a process in which longer-chain hydrocarbons are produced from oil and fuels via olefins.

For thermal steamcracking, cracking furnaces are used. The cracking furnaces, together with a quench unit and downstream devices for processing of the product mixtures formed, are integrated into corresponding larger plants for olefin production, which are referred to in the context of this application as "steamcrackers".

An important parameter in thermal steamcracking is the cracking severity, which determines the cracking conditions. The cracking conditions are influenced especially by the temperature and residence time and the partial pressures of the hydrocarbons and of the steam. The composition of the hydrocarbon mixtures used as the feed and the design of the cracking furnaces used also influence the cracking conditions. Because of the mutual influences of these factors, the cracking conditions are normally defined via the ratio of propylene (also referred to as propene) to ethylene in the cracking gas.

According to the feed mixture and cracking conditions, thermal steamcracking gives rise not only to ethylene, the standard target compound, but also to sometimes considerable amounts of by-products, which can be separated from a corresponding product stream. These include lower alkenes, for example propylene and butenes, and also dienes, for example butadienes, and also aromatics, for example benzene, toluene and xylenes. These are of comparatively high economic value, and so the formation thereof as "high-value products" is desirable.

The problem addressed by the present invention is therefore that of improving the means of obtaining olefin-containing product mixtures from hydrocarbons by thermal steamcracking.

DISCLOSURE OF THE INVENTION

Against this background, the invention proposes a process for converting feeds composed of hydrocarbons by thermal steamcracking to at least one olefin-containing product stream comprising at least ethylene and propylene, with at least partial conversion of the feeds in at least one first cracking furnace and in at least one second cracking furnace, having the features of the independent claims. Preferred configurations are the subject of the dependent claims and of the description which follows.

ADVANTAGES OF THE INVENTION

According to the invention, a process is proposed in which a fresh feed is fractionated into at least one first and one second fresh feed fraction of different composition, and the first fresh feed fraction is conducted at least partly, preferably fully, into the first cracking furnace and the second fresh feed fraction at least partly, preferably fully, into the second cracking furnace.

A cracking furnace is understood in the context of this invention to mean a cracking unit in which the cracking conditions are defined. It is possible that a subdivision into two or more cracking furnaces is present in one overall furnace. In that case, reference is frequently made to furnace cells. A plurality of furnace cells forming part of an overall furnace generally have independent radiation zones and a common convection zone, and also a common smoke outlet. In these cases, each furnace cell can be operated with its own cracking conditions. Each furnace cell is thus a cracking unit and is consequently referred to here as a cracking furnace. In that case, the overall furnace has a plurality of cracking units or, in other words, it has a plurality of cracking furnaces. If only one furnace cell is present, this is the cracking unit and hence the cracking furnace. Cracking furnaces can be combined to form groups, which are supplied, for example, with the same feed. The cracking conditions within a furnace group are generally adjusted to be the same or similar.

According to the invention, the first and second fresh feed fractions have a different composition. It is thus emphasized that the division of the fresh feed is a fractionation and not a simple division into two amounts. In a fractionation, a separation is effected according to different components. After the fractionation, some components of the fresh feed are thus present predominantly in the first fresh feed fraction, and other components of the fresh feed are present predominantly in the second fresh feed fraction.

The thermal cracking of hydrocarbons of typical composition, for example naphtha, under mild cracking conditions gives rise to a very large amount of pyrolysis gasoline, which is very difficult to deal with because of the large amount. This is a result of the comparatively lower conversion of the feed in the cracking furnace under mild cracking conditions. Mild cracking conditions, however, are desirable since more propylene in relation to the fresh feed is formed in the case of cracking under mild conditions than in the case of cracking under normal cracking conditions as typically used. As a result of the inventive fractionation of the fresh feed and controlled conduction into assigned cracking furnaces, the fresh feed is divided in such a way that cracking can be performed under mild cracking conditions in at least one cracking furnace and cracking can be performed under standard cracking conditions in at least one cracking furnace, without formation of excessively large amounts of pyrolysis gasoline. Instead, the amounts of pyrolysis gasoline remain controllable. The process according to the invention thus makes it possible to operate a steamcracking plant in such a way that more propylene is formed in relation to the fresh feed than in a conventional plant in which the process according to the invention is not used. In the context of the invention, this problem and the solution proposed have been recognized.

The inventive fractionation of the fresh feed and controlled conduction into assigned cracking furnaces make it possible to divide the fresh feed in a controlled manner, such that cracking furnace feed and cracking conditions can be matched to one another optimally. At first glance, it appears senseless to undertake a fractionation of the fresh feed, since this is associated with considerable apparatus complexity and consequently with high capital costs. However, it has been found that, surprisingly, the advantages established because of the matching of cracking furnace feed and cracking conditions which is now possible by far outweigh the disadvantages.

The procedures which are needed to fractionate the fresh feed are known to those skilled in the art. These are measures customary in steamcrackers for separation and processing of product and fraction streams, which are matched to the specific properties of the fresh feed.

Particularly advantageously, the second fresh feed fraction comprises predominantly hydrocarbons having a maximum carbon number of 5. More particularly, the second fresh feed fraction comprises predominantly hydrocarbons having a carbon number of 5 and/or 4.

In addition, the first fresh feed fraction advantageously comprises predominantly hydrocarbons having a carbon number of at least 6.

If the fresh feed is divided in such a way, it is possible to operate a plant for steamcracking in a very particularly advantageous manner, and much more propylene in relation to the fresh feed is formed than in a conventional plant.

The word "predominantly" is used in the context of this application to make it clear that the feed or the fraction does not consist exclusively of hydrocarbons having the specified carbon number, but that hydrocarbons having other carbon numbers and other impurities may also be present alongside the hydrocarbons of the specified carbon number. The separation and processing of the fresh feed, of the product stream and/or the fractions always leaves residues of the component (s) in the product stream or in the fraction. Other impurities also persist, and so a processed product stream or fraction stream always contains residues. Since the cost and inconvenience associated with separation and processing rise to an extremely high degree with the purity to be achieved, economic factors decide what proportion of residues may be present in a stream. The level of this proportion has to be weighed up according to economic considerations. A rough guide value for the proportion of unwanted hydrocarbons and other impurities will generally be that not more than 30 to 40 percent by weight may be present in the product stream and/or in the fraction. Usually, a maximum value of 15 percent by weight or less is actually attained. The fresh feed fractions thus contain the desired hydrocarbons at at least 60 percent by weight, preferably at least 80 percent by weight and further preferably at least 90 percent by weight and more preferably at least 95 percent by weight and most preferably at least 98 percent by weight. The limits just stated also apply to the recycled fractions (see below).

Advantageously, cracking conditions that lead to a ratio of propylene to ethylene of 0.7 to 1.6 kg/kg, preferably of 0.8 to 1.4 kg/kg and more preferably of 0.85 to 1.2 kg/kg at the cracking furnace exit exist in the second cracking furnace. If the feed is converted under mild cracking conditions, the aforementioned advantages of the invention are manifested particularly markedly. Also advantageous are cracking conditions that lead to a ratio of propylene to ethylene at the cracking furnace exit of 0.75 to 1.5 kg/kg or of 0.8 to 1.2 kg/kg or of 0.85 to 1.15 kg/kg, or which are even within the narrow range of 0.9 to 1.1 kg/kg.

It is additionally advantageous when cracking conditions that lead to a ratio of propylene to ethylene of 0.25 to 0.85 kg/kg, preferably of 0.3 to 0.75 kg/kg and more preferably of 0.4 to 0.65 kg/kg at the cracking furnace exit exist in the first cracking furnace, the values attained for the ratio of propylene to ethylene in the second cracking furnace being above those in the first cracking furnace.

The operation of at least two cracking furnaces under the various cracking conditions just specified achieves very particular advantages, since the cracking conditions in the two cracking furnaces can be matched to the respective feed. For instance, it is a feature of the cracking conditions in the second cracking furnace that they can be used to achieve the very high values specified for the ratio of propylene to ethylene. In the first cracking furnace, in contrast, the feed is converted under standard cracking conditions. The matching of the cracking conditions to the respective feed achieves the effect that the pyrolysis gasoline fraction remains controllable in terms of amount. Smaller amounts of pyrolysis oil are also formed in the second cracking furnace under mild conditions than in the first cracking furnace, but the amounts of pyrolysis oil formed in the first cracking furnace too are controllable.

The values attained for the ratio of propylene to ethylene in the second cracking furnace are advantageously at least 0.1 kg/kg above, preferably at least 0.15 kg/kg above and more preferably at least 0.2 kg/kg above those in the first cracking furnace.

In a particularly advantageous configuration of the invention, one or more fractions which are obtained from the product stream and which comprise hydrocarbons having a maximum carbon number of 5 are recycled into the second cracking furnace. This has the advantage that the amount of feed which is conducted into the at least one second cracking furnace is increased. This recycled fraction is chosen such that it promotes the advantages of the process according to the invention because of its composition. This promotion is particularly marked for fractions comprising hydrocarbons having a carbon number of 5 and/or 4.

In addition, it is advantageous when one or more fractions which are obtained from the product stream and which comprise hydrocarbons having a carbon number of at least 6 are recycled into the first cracking furnace. Because of their composition, such fractions can be cracked efficiently in the first cracking furnace to give products of value.

In a further advantageous configuration of the invention, the second cracking furnace is supplied not only with the second fresh feed fraction but also with a further fresh feed consisting predominantly of hydrocarbons having a maximum carbon number of 5. Such a further fresh feed can be obtained, for example, in a refinery or in natural gas production. Because of its characteristics, it is of very good suitability as a feed in the second cracking furnace under mild cracking conditions. In addition, it may likewise be advantageous to add not only the first fresh feed fraction but also a further fresh feed to the first cracking furnace.

As explained at the outset, the ratio of propylene to ethylene in the thermal steamcracking operation results from a number of different influencing factors, among which the cracking furnace exit temperature, i.e. the temperature of a product stream on departure from the reactor coil used (coil output temperature), plays an important role. The cracking furnace exit temperature for the conversion in the second cracking furnace is advantageously between 680° C. and 820° C., preferably between 700° C. and 800° C. and further preferably between 710° C. and 780° C. and more preferably between 720° C. and 760° C., while the cracking furnace exit temperature for the conversion in the first cracking furnace is advantageously between 800° C. and 1000° C., preferably between 820° C. and 950° C. and more preferably between 840° C. and 900° C. The cracking furnace exit temperature in the first cracking furnace is always higher than in the second cracking furnace.

The cracking furnace exit temperature for the conversion in the first cracking furnace is preferably at least 10° C. above, more preferably at least 15° C. above and most preferably at least 20° C. above the cracking furnace exit temperature for the conversion in the second cracking furnace.

In the second cracking furnace, a lower steam dilution than in the first can also be used. This reduces the amount of dilution steam needed and saves energy. However, a lower steam dilution in the second cracking furnace is unnecessary for the significant advantages of the invention to be manifested. Advantageously, in the second cracking furnace 0.15 to 0.8 kg of steam per kg of hydrocarbon is used in the feed, whereas in the first cracking furnace 0.3 to 1.5 kg of steam per kg of hydrocarbon is used in the feed.

It is also advantageously possible to convert especially saturated hydrocarbons having a carbon number of 2 to 3 present in the product stream by means of thermal steamcracking in a cracking furnace for gaseous feed. To this end, the saturated gaseous hydrocarbons are obtained from the product stream, and recycled into and converted in the cracking furnace for gaseous feed.

The fresh feeds used for the fresh feed fractionation may be either gases or gas fractions, such as ethane, propane or butane, and corresponding mixtures and condensates, or liquid hydrocarbons and hydrocarbon mixtures. These gas mixtures and condensates comprise especially what are called natural gas condensates (natural gas liquids, NGL). The liquid hydrocarbons and hydrocarbon mixtures may originate, for example, from what is called the gasoline fraction of crude oil. Such crude gasolines or naphthas (NT) and kerosene are mixtures of preferably saturated compounds having boiling points between 35 and 210° C.

Very particularly advantageous fresh feeds are liquid hydrocarbons. More particularly, the fresh feeds used are natural gas condensates and/or crude oil fractions and/or mixtures derived therefrom.

Advantageously, the invention thus encompasses the use of hydrocarbon mixtures having a boiling range of up to 600° C. as fresh feed. Within this overall range, it is also possible to use hydrocarbon mixtures having different boiling ranges, for example having boiling ranges of up to 360° C. or of up to 240° C. The reaction conditions in the cracking furnace are matched here to the hydrocarbon mixtures used in each case.

For instance, the invention can, however, also be used advantageously with any desired fresh feeds having comparable properties, for example biogenic or/and synthetic hydrocarbons.

BRIEF DESCRIPTION OF THE DRAWING

The process according to the invention in a particularly advantageous configuration is to be elucidated in detail with reference to the process flow diagrams which show the essential process steps in schematic form. For better understanding, the known process is first illustrated with reference to FIG. 1.

Figure 1:
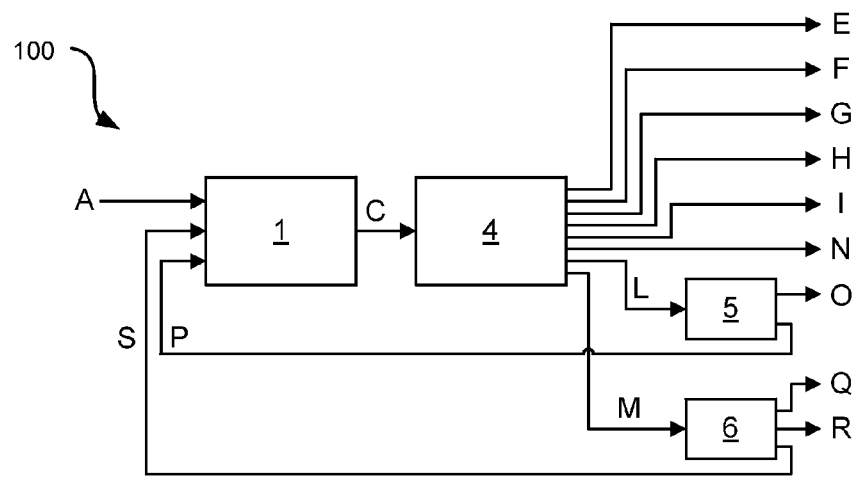
FIG. 1 shows to this end a schematic view of a known method for olefin production.

The schematic process flow diagram 100 of FIG. 1 for the known process includes a cracking furnace 1 into which the fresh feed A (for example naphtha) and the recycled fractions S and P as hydrocarbon feeds are conducted. In the cracking furnace 1, the hydrocarbon feed is heated and converted in convection and radiation zones. Steam is added to the cracking furnace, usually 0.5 to 1 kg of process steam per kg of hydrocarbon. A product stream C emerges from the cracking furnace 1, and this is also referred to as the cracking product stream directly at the exit from the cracking furnace. On exit from the cracking furnace, this cracking product stream has a temperature normally between 840° C. and 900° C. The ratio of propylene to ethylene is generally 0.35 to 0.6 kg/kg. After a first quench (not shown), the product stream is processed in a processing unit 4. From the processing unit, the following fractions are obtained as essential product fractions E to N: hydrogen E, waste liquor F, methane G, ethylene H, propylene I, gaseous hydrocarbons L having a carbon number of 4, pyrolysis gasoline M and pyrolysis oil N. The gaseous hydrocarbons L having a carbon number of 4 are treated further in a C4 processing unit 5, which is utilized for the processing of hydrocarbons having a carbon number of 4. Such a C4 processing unit 5 treats the fraction having a carbon number of 4 further in such a way that butadiene O can be removed. The other hydrocarbons having a carbon number of 4 constitute a fraction P which is recycled into the cracking furnace 1. The pyrolysis gasoline M comprising hydrocarbons having a carbon number of 5 or more is processed further in a pyrolysis gasoline processing unit 6, and aromatics Q and hydrocarbons R having a carbon number of, for example, more than 9 are removed. The other hydrocarbons having a carbon number of 5 or more are recycled as fraction S into the cracking furnace 1. The processing unit 4, and also the C4 processing unit 5 and the pyrolysis gasoline processing unit 6, comprise customary units for further processing of the product stream or of the product fractions, which serve to execute various process steps, for example compression, condensation and cooling, drying, distillation and fractionation, extraction and hydrogenation. The process steps are customary in olefin plants are known to those skilled in the art.

Figure 2:
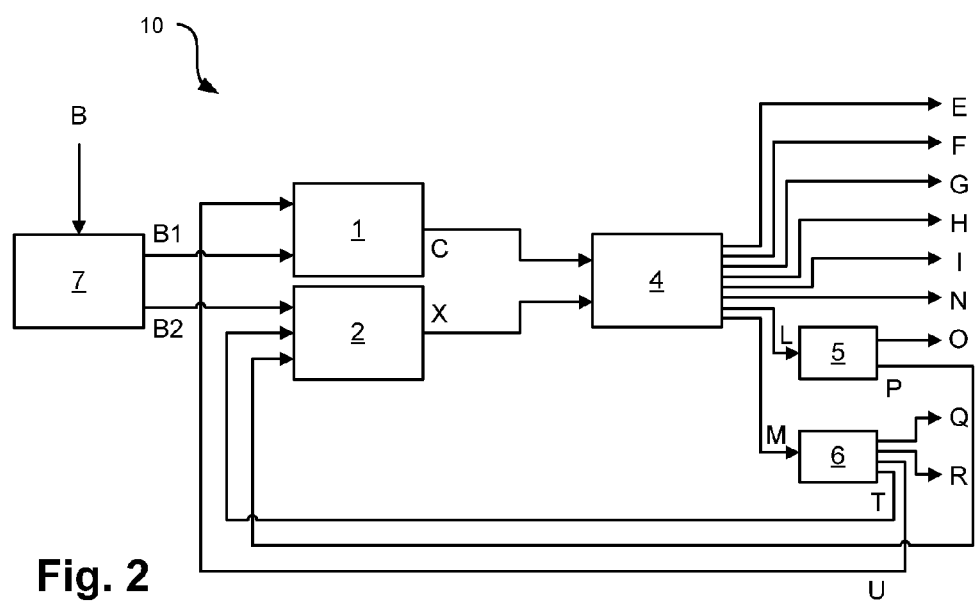
FIG. 2 shows a schematic view of the essential steps of the process according to the invention in a particularly advantageous configuration.

The schematic process flow diagram 10 of FIG. 2 then shows the process according to the invention in a particularly advantageous configuration, and the essential process steps thereof. In addition to the cracking furnace 1, a second cracking furnace 2 is present here, as is a fresh feed fractionation unit 7. A fresh feed B (for example naphtha) is then fractionated in the fresh feed fractionation unit 7 and the first fresh feed fraction B1 is conducted into the first cracking furnace 1, while the second fresh feed fraction B2 is conducted into the second cracking furnace 2. For the processes for fractionation of the fresh feed, the customary methods for separation and treatment of hydrocarbon streams are used, as known from olefin plants from refineries. The person skilled in the art knows of these, and how to use them. Advantageously, a fraction U is additionally recycled into the first cracking furnace 1, and the fractions T and P are additionally recycled into the second cracking furnace 2 (for further details see below). In turn, the cracking product stream C having the abovementioned properties emerges from the first cracking furnace 1. The cracking product stream X emerges from the second cracking furnace 2. The cracking product stream X is at a temperature advantageously between 700° C. and 800° C. The ratio of propylene to ethylene therein is advantageously between 0.7 and 1.5 kg/kg. The product streams C and X are processed further in the processing unit 4 and combined at a suitable point to give a common product stream. The processes for further treatment and processing in the processing unit 4 are known and have just been described. Thus, the processing unit 4 also leads, as just described, to the product fractions E to N. The product fractions L and M too, as just, are treated further in the specific processing units 5 and 6. In contrast to the process described in FIG. 1, the fraction P comprising hydrocarbons having a carbon number of 4 is then advantageously also recycled not into the cracking furnace 1 but into the second cracking furnace 2. In the pyrolysis gasoline processing unit 6, as well as the abovementioned fractions Q and R, the fractions T and U are obtained. The fraction T comprising hydrocarbons having a carbon number of 5 is advantageously recycled into the second cracking furnace 2, while the fraction U comprising hydrocarbons having a carbon number of 6 or more, especially between 6 and 9, is advantageously recycled into the first cracking furnace 1.

Figure 3:
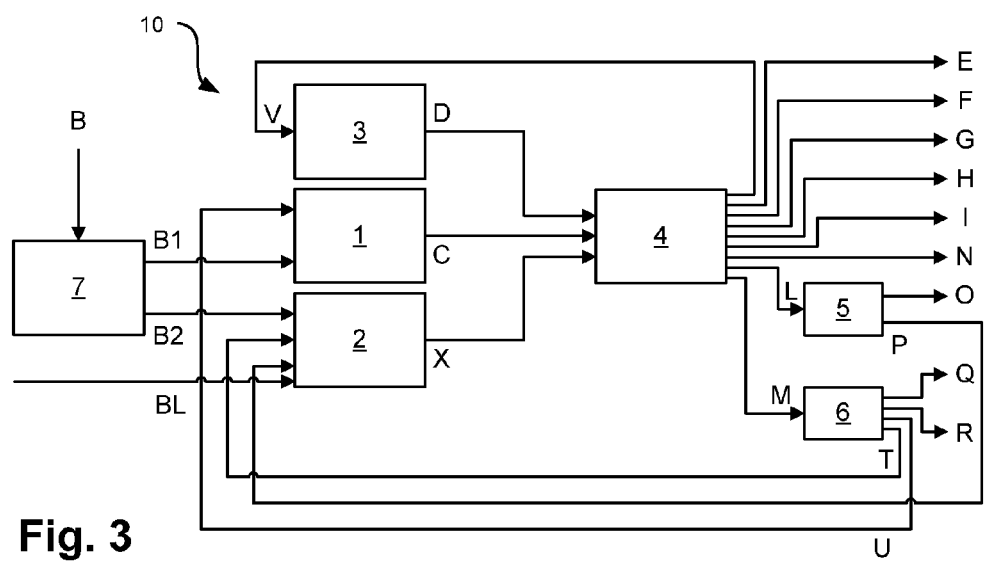
FIG. 3 shows, likewise in schematic form, the essential steps of a particularly advantageous configuration of the invention. In the figures, corresponding elements bear identical reference numerals.

A particularly advantageous configuration of the invention includes FIG. 3. FIG. 3 has the same schematic process flow diagram as also shown in FIG. 2. This is supplemented by a cracking furnace 3 for gaseous feed, into which a fraction V is conducted as feed. The fraction V comprises saturated gaseous hydrocarbons having a carbon number of 2 or 3, which are likewise obtained in the processing unit 4. In addition, a further fresh feed BL consisting predominantly of hydrocarbons having a maximum carbon number of 5 is also supplied here to the second cracking furnace 2.

LIST OF REFERENCE NUMERALS

1 cracking furnace (normal cracking conditions)
2 cracking furnace (mild cracking conditions)
3 cracking furnace for gaseous feed
4 processing unit
5 C4 processing unit
6 pyrolysis gasoline processing unit
7 fresh feed fractionation unit
10 schematic process flow diagram for a known process
100 schematic process flow diagram for the process according to the invention in a particularly advantageous configuration
A, B, BL fresh feed
B1, B2 fresh feed fractions
C, D, X product streams
E-V product fractions

The invention claimed is:

1. A process for converting feeds composed of hydrocarbons by thermal steamcracking to at least one olefin-containing product stream comprising at least ethylene and propylene, with at least partial conversion of the feeds in at least one first cracking furnace (1) and in at least one second cracking furnace (2), wherein a fresh feed (B) is fractionated into at least one first and one second fresh feed fraction (B1, B2) of different composition and the first fresh feed fraction (B1) is conducted at least partly into the first cracking furnace (1) and the second fresh feed fraction (B2) at least partly into the second cracking furnace (2), characterized in that the second fresh feed fraction (B2) comprises predominantly hydrocarbons having a maximum carbon number of 5, in that the first fresh feed fraction (B1) comprises predominantly hydrocarbons having a carbon number of at least 6, in that cracking conditions that lead to a ratio of propylene to ethylene of 0.7 to 1.6 kg/kg at the cracking furnace exit exist in the second cracking furnace (2), and in that cracking conditions that lead to a ratio of propylene to ethylene of 0.25 to 0.85 kg/kg at the cracking furnace exit exist in the first cracking furnace (1), the values attained for the ratio of propylene to ethylene in the second cracking furnace (2) being above those in the first cracking furnace (1).

2. The process as claimed in claim 1, characterized in that cracking conditions that lead to a ratio of propylene to ethylene of 0.8 to 1.4 kg/kg and preferably of 0.85 to 1.2 kg/kg at the cracking furnace exit exist in the second cracking furnace (2).

3. The process as claimed in claim 1, characterized in that cracking conditions that lead to a ratio of propylene to ethylene of 0.3 to 0.75 kg/kg and preferably of 0.4 to 0.65 kg/kg at the cracking furnace exit exist in the first cracking furnace (1).

4. The process as claimed in claim 1, in which the values attained for the ratio of propylene to ethylene in the second cracking furnace (2) are at least 0.1 kg/kg above, preferably at least 0.15 kg/kg above and more preferably at least 0.2 kg/kg above those in the first cracking furnace (1).

5. The process as claimed in claim 1, characterized in that one or more fractions (P, T) which are obtained from the product stream and which comprise hydrocarbons having a maximum carbon number of 5 are recycled into the second cracking furnace (2).

6. The process as claimed in claim 1, characterized in that one or more fractions (U) which are obtained from the product stream and which comprise hydrocarbons having a carbon number of at least 6 are recycled into the first cracking furnace (1).

7. The process as claimed in claim 1, characterized in that the second cracking furnace (2) is supplied not only with the second fresh feed fraction (B2) but also with a further fresh feed (BL) consisting predominantly of hydrocarbons having a maximum carbon number of 5.

8. The process as claimed in claim 1, in which the cracking furnace exit temperature for the conversion in the second cracking furnace (2) is between 680° C. and 820° C., preferably between 700° C. and 800° C. and further preferably between 710° C. and 780° C. and more preferably between 720° C. and 760° C., and the cracking furnace exit temperature for the conversion in the first cracking furnace (1) is between 800° C. and 1000° C., preferably between 820° C. and 950° C. and more preferably between 840° C. and 900° C., the cracking furnace exit temperature of the first cracking furnace (1) being above that of the second cracking furnace (2).

9. The process as claimed in claim 8, in which the cracking furnace exit temperature for the conversion in the first cracking furnace (1) is at least 10° C. above, preferably at least 15° C. above, more preferably at least 20° C. above, the cracking furnace exit temperature for the conversion in the second cracking furnace (2).

10. The process as claimed in claim 1, in which 0.3 to 1.5 kg of steam per kg of hydrocarbon feed is used in the first cracking furnace (1), and 0.15 to 0.8kg of steam per kg of hydrocarbon feed in the second cracking furnace (2).

11. The process as claimed in claim 1, in which at least one fraction (V) comprising predominantly hydrocarbons having a carbon number of 2 or 3 is obtained from the product stream and at least partly converted in a cracking furnace (3) for gaseous feed.

12. The process as claimed in any of claim 1, characterized in that the fresh feed (B) used comprises natural gas condensates and/or crude oil fractions, especially naphtha, and/or synthetic and/or biogenic hydrocarbons and/or mixtures derived therefrom.

* * * * *